United States Patent
Litvak et al.

(10) Patent No.: US 9,479,877 B2
(45) Date of Patent: Oct. 25, 2016

(54) METHODS AND SYSTEMS FOR LOGGING DATA ASSOCIATED WITH AN OPERATION OF A SOUND PROCESSOR BY AN AUDITORY PROSTHESIS

(75) Inventors: Leonid M. Litvak, Los Angeles, CA (US); Lakshmi N. Mishra, Valencia, CA (US)

(73) Assignee: Advanced Bionics AG, Staefa (CH)

( * ) Notice: Subject to any disclaimer, the term of this patent is extended or adjusted under 35 U.S.C. 154(b) by 192 days.

(21) Appl. No.: 14/126,338

(22) PCT Filed: Jun. 8, 2012

(86) PCT No.: PCT/US2012/041645
§ 371 (c)(1),
(2), (4) Date: Dec. 13, 2013

(87) PCT Pub. No.: WO2012/177424
PCT Pub. Date: Dec. 27, 2012

(65) Prior Publication Data
US 2014/0126731 A1 May 8, 2014

Related U.S. Application Data

(60) Provisional application No. 61/499,628, filed on Jun. 21, 2011.

(51) Int. Cl.
*H04R 29/00* (2006.01)
*H04R 25/00* (2006.01)
*A61N 1/36* (2006.01)
*A61N 1/372* (2006.01)

(52) U.S. Cl.
CPC .......... *H04R 25/30* (2013.01); *A61N 1/36032* (2013.01); *A61N 1/37252* (2013.01); *H04R 25/305* (2013.01); *H04R 25/70* (2013.01); *H04R 2225/39* (2013.01); *H04R 2225/67* (2013.01)

(58) Field of Classification Search
CPC .... H04R 25/30; H04R 25/305; H04R 25/70; H04R 25/55; H04R 25/606; H04R 2225/39; H04R 2225/55; H04R 2225/67
USPC .......... 381/60, 312, 331; 600/25; 607/55, 57
See application file for complete search history.

(56) References Cited

U.S. PATENT DOCUMENTS

| | | | |
|---|---|---|---|
| 4,972,487 A | 11/1990 | Mangold et al. | |
| 6,334,072 B1 * | 12/2001 | Leysieffer | 607/57 |
| 7,242,777 B2 | 7/2007 | Leenen et al. | |
| 7,801,616 B2 | 9/2010 | De Paep | |

(Continued)

OTHER PUBLICATIONS

International Search Report and Written Opinion received in International Application No. PCT/US12/041645 dated Aug. 20, 2012.

(Continued)

*Primary Examiner* — Xu Mei
(74) *Attorney, Agent, or Firm* — ALG Intellectual Property, LLC

(57) ABSTRACT

An exemplary method includes 1) detecting, by an auditory prosthesis configured to be implanted in a patient, a communicative coupling of a sound processor to the auditory prosthesis, the sound processor configured to be located external to the patient, and 2) logging, by the auditory prosthesis, data associated with an operation of the sound processor while the sound processor is communicatively coupled to the auditory prosthesis. Corresponding auditory prostheses and systems are also disclosed.

17 Claims, 5 Drawing Sheets

(56) References Cited

U.S. PATENT DOCUMENTS

| | | |
|---|---|---|
| 8,077,889 B2 | 12/2011 | Bachler et al. |
| 8,077,892 B2 | 12/2011 | Dijkstra et al. |
| 2004/0024429 A1* | 2/2004 | Daly ............................... 607/59 |
| 2004/0202340 A1* | 10/2004 | Armstrong et al. .......... 381/312 |
| 2005/0129262 A1* | 6/2005 | Dillon et al. ................. 381/312 |
| 2006/0222194 A1* | 10/2006 | Bramslow et al. ........... 381/314 |
| 2007/0027676 A1* | 2/2007 | Chambers et al. ........ 704/200.1 |
| 2007/0260292 A1* | 11/2007 | Faltys et al. ................... 607/57 |
| 2008/0260190 A1* | 10/2008 | Kidmose ....................... 381/314 |
| 2010/0016922 A1* | 1/2010 | Daly ............................... 607/57 |
| 2011/0060383 A1* | 3/2011 | Lineaweaver et al. ......... 607/57 |
| 2011/0098786 A1 | 4/2011 | Mishra et al. |

OTHER PUBLICATIONS

Communication pursuant to Article 94(3) EPC received in European Patent Application No. 12727762.2, dated Oct. 13, 2014.

\* cited by examiner

METHODS AND SYSTEMS FOR LOGGING DATA ASSOCIATED WITH AN OPERATION OF A SOUND PROCESSOR BY AN AUDITORY PROSTHESIS

RELATED APPLICATIONS

The present application claims priority to U.S. Provisional Patent Application No. 61/499,628 by Leonid M. Litvak et al., filed on Jun. 21, 2011, and entitled "METHODS AND SYSTEMS FOR LOGGING DATA ASSOCIATED WITH AN OPERATION OF A SOUND PROCESSOR BY AN AUDITORY PROSTHESIS," the contents of which are hereby incorporated by reference in their entirety.

BACKGROUND INFORMATION

The sense of hearing in human beings involves the use of hair cells in the cochlea that convert or transduce audio signals into auditory nerve impulses. Hearing loss, which may be due to many different causes, is generally of two types: conductive and sensorineural. Conductive hearing loss occurs when the normal mechanical pathways for sound to reach the hair cells in the cochlea are impeded. These sound pathways may be impeded, for example, by damage to the auditory ossicles. Conductive hearing loss may often be helped by the use of conventional hearing aids that amplify sound so that audio signals reach the cochlea and the hair cells. Some types of conductive hearing loss may also be treated by surgical procedures.

Sensorineural hearing loss, on the other hand, is caused by the absence or destruction of the hair cells in the cochlea which are needed to transduce acoustic signals into auditory nerve impulses. People who suffer from sensorineural hearing loss may be unable to derive significant benefit from conventional hearing aid systems, no matter how loud the acoustic stimulus is. This is because the mechanism for transducing sound energy into auditory nerve impulses has been damaged. Thus, in the absence of properly functioning hair cells, auditory nerve impulses cannot be generated directly from sounds.

To overcome sensorineural hearing loss, numerous auditory prosthesis systems (e.g., cochlear implant systems) have been developed. A typical auditory prosthesis system includes a sound processor configured to be located external to a patient and an auditory prosthesis configured to be implanted within the patient. The sound processor is configured to process audio signals presented to the patient and direct the auditory prosthesis to generate and apply electrical stimulation representative of the audio signals directly to stimulation sites (e.g., auditory nerve fibers) within the patient by way of one or more channels formed by an array of electrodes. Direct stimulation of the stimulation sites leads to the perception of sound in the brain and at least partial restoration of hearing function.

It is often desirable to log data associated with an operation of a sound processor included in an auditory prosthesis system. For example, statistics such as use of volume control, battery life, usage time, sound levels, and other data associated with the sound processor may be useful in order to assess a performance of the sound processor, adjust one or more control parameters governing an operation of the sound processor, and/or otherwise adjust a manner in which the sound processor operates. Such logging has typically been done by the speech processor itself. However, some patients utilize more than one sound processor. For example, a patient may have two sound processors that he or she interchangeably uses in connection with his or her auditory prosthesis. Unfortunately, the logging data acquired by each sound processor cannot be shared between the two sound processors. Hence, each sound processor cannot optimize its respective operation based on all of the logging data acquired by both sound processors.

SUMMARY

An exemplary method includes 1) detecting, by an auditory prosthesis configured to be implanted in a patient, a communicative coupling of a sound processor to the auditory prosthesis, the sound processor configured to be located external to the patient, and 2) logging, by the auditory prosthesis, data associated with an operation of the sound processor while the sound processor is communicatively coupled to the auditory prosthesis.

An exemplary auditory prosthesis configured to be implanted in a patient includes 1) a detection facility configured to detect a communicative coupling of a sound processor to the auditory prosthesis, the sound processor located external to the patient, and 2) a data logging facility communicatively coupled to the detection facility and configured to log data associated with an operation of the sound processor while the sound processor is communicatively coupled to the auditory prosthesis.

An exemplary system includes 1) a sound processor configured to be located external to a patient and operate in accordance with one or more control parameters and 2) an auditory prosthesis communicatively coupled to the sound processor and configured to be implanted within the patient. The auditory prosthesis is further configured to detect a communicative coupling of the sound processor to the auditory prosthesis and log data associated with an operation of the sound processor while the sound processor is communicatively coupled to the auditory prosthesis.

BRIEF DESCRIPTION OF THE DRAWINGS

The accompanying drawings illustrate various embodiments and are a part of the specification. The illustrated embodiments are merely examples and do not limit the scope of the disclosure. Throughout the drawings, identical or similar reference numbers designate identical or similar elements.

DETAILED DESCRIPTION

Figure 1:
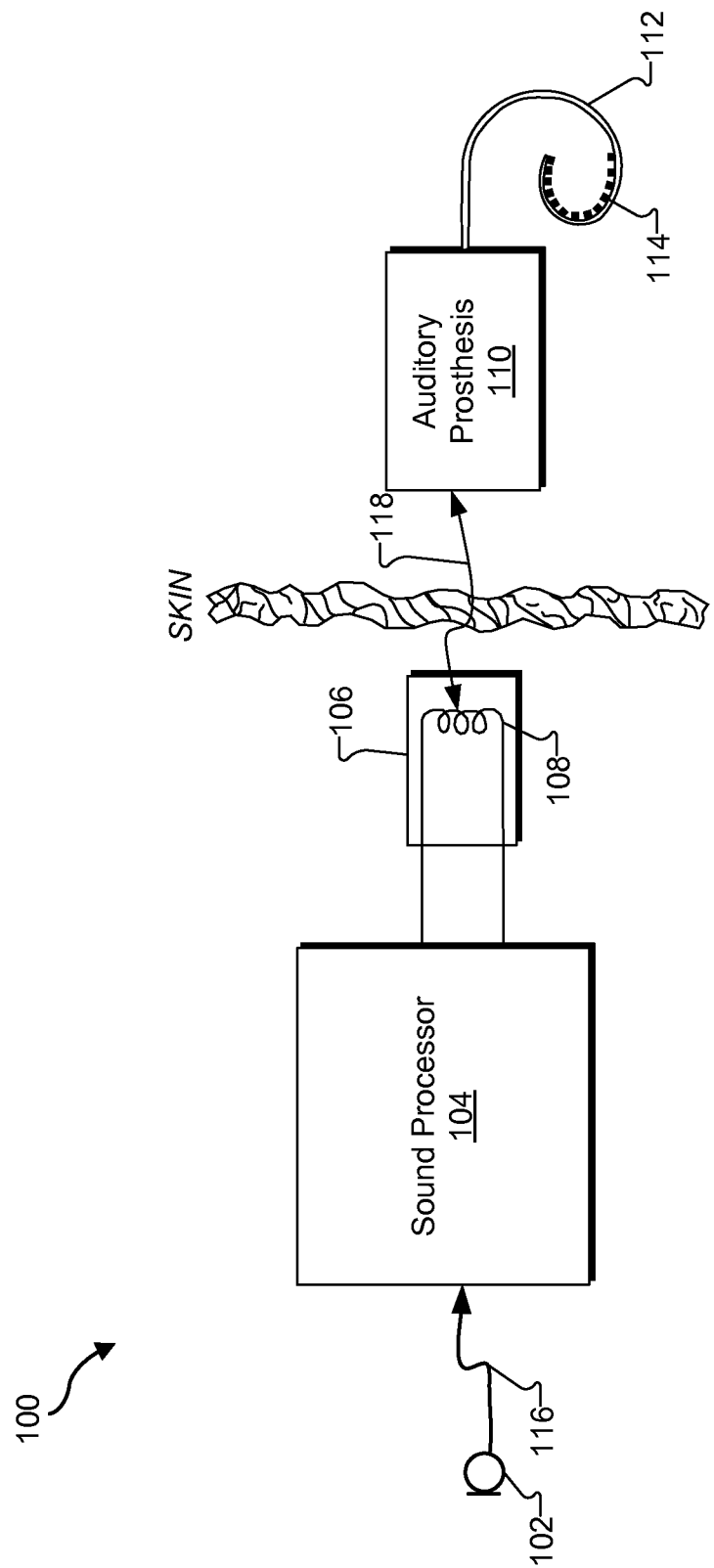
FIG. 1 illustrates an exemplary auditory prosthesis system according to principles described herein.

Methods and systems for logging data associated with an operation of a sound processor by an auditory prosthesis are described herein. As will be described below, an auditory prosthesis configured to be implanted in a patient may detect a communicative coupling of a sound processor to the auditory prosthesis. The auditory prosthesis may then log data associated with an operation of the sound processor while the sound processor is communicatively coupled to the auditory prosthesis.

Various advantages are associated with logging data with the auditory prosthesis (as opposed to the sound processor). For example, in cases where a patient uses multiple sound processors, all of the logging data associated with an operation of each of the sound processors may be maintained in a single location (i.e., within an auditory prosthesis implanted within the patient). The logging data may then be utilized by whichever sound processor is communicatively coupled to the auditory prosthesis at a given time, thereby increasing the amount of data upon which the sound processors may rely in order to adjust one or more control parameters and/or perform any other function. Additionally or alternatively, the logging data maintained by the auditory prosthesis may be used by a fitting device or other computing device communicatively coupled to the auditory prosthesis by way of one or more of the sound processors in order to compare a relative effectiveness of each of the sound processors.

As used herein, the terms "log data," "logged data," and "logging data" will be used interchangeably to refer to data that may be logged by an auditory prosthesis. The log data may be associated with an operation of a sound processor and/or the auditory prosthesis. For example, the log data may include volume control data (e.g., data representative of various volume levels specified by a patient), battery life data (e.g., data representative of a remaining battery life of the sound processor and/or auditory prosthesis), usage time data (e.g., data representative of an amount of time that the sound processor is communicatively coupled to the auditory prosthesis), sound level data (e.g., data representative of one or more sound levels associated with a particular sound processing program executed by the sound processor), sound processing program usage data (e.g., data representative of an amount of time that one or more sound processing programs are used by a patient), measurement data (e.g., electrode impedance data, neural response imaging data, electrical field imaging data), testing data (e.g., data resulting from one or more testing procedures performed by a fitting device and/or the sound processor), troubleshooting data (e.g., data associated with a testing of the sound processor and/or auditory prosthesis data), acoustic scene data (e.g., data representative of a particular scene or environment in which the patient is located), operating status data (e.g., data representative of an operating status of the sound processor and/or auditory prosthesis), and/or control parameter data (e.g., data representative of one or more control parameters associated with a sound processing program being executed by the sound processor).

To facilitate an understanding of the methods and systems described herein, an exemplary auditory prosthesis system 100 will be described in connection with FIG. 1. As shown in FIG. 1, auditory prosthesis system 100 may include a microphone 102, a sound processor 104, a headpiece 106 having a coil 108 disposed therein, an auditory prosthesis 110, and a lead 112 with a plurality of electrodes 114 disposed thereon. Additional or alternative components may be included within auditory prosthesis system 100 as may serve a particular implementation.

As shown in FIG. 1, microphone 102, sound processor 104, and headpiece 106 may be located external to an auditory prosthesis patient, and auditory prosthesis 110, lead 112, electrodes 114 may be implanted subcutaneously with the patient. In some alternative examples, microphone 102 and/or sound processor 104 may also be implanted within the patient. In such configurations, the need for headpiece 106 may be obviated.

Microphone 102 may detect an audio signal and convert the detected signal to a corresponding electrical signal. The electrical signal may be sent from microphone 102 to sound processor 104 via a communication link 116, which may include a telemetry link, a wire, and/or any other suitable communication link.

Sound processor 104 is configured to direct auditory prosthesis 110 to generate and apply electrical stimulation (also referred to herein as "stimulation current") to one or more stimulation sites within a cochlea of the patient. To this end, sound processor 104 may process the audio signal detected by microphone 102 in accordance with a selected sound processing program loaded on sound processor 104 to generate appropriate stimulation parameters for controlling auditory prosthesis 110. In certain examples, sound processor may 104 may include multiple sound processing programs loaded thereon such that a patient may select, from the multiple sound processing programs, which sound processing program to utilize to generate stimulation parameters. Accordingly, the patient may select a sound processing program that is well suited for a particular situation.

Sound processor 104 may include or be implemented by a behind-the-ear ("BTE") unit, an off-the-ear speech processor (i.e., a speech processor configured to be worn off the ear, such as a portable speech processor ("PSP")), and/or any other sound processing unit as may serve a particular implementation. Exemplary components of sound processor 104 will be described in more detail below.

Sound processor 104 may be configured to transcutaneously transmit one or more control parameters and/or one or more power signals to auditory prosthesis 110 with coil 108 by way of a communication link 118. These control parameters may be configured to specify one or more stimulation parameters, operating parameters, and/or any other parameter by which auditory prosthesis 110 is to operate as may serve a particular implementation. Exemplary control parameters include, but are not limited to, stimulation current levels, volume control parameters, program selection parameters, operational state parameters (e.g., parameters that turn a sound processor and/or an auditory prosthesis on or off), audio input source selection parameters, fitting parameters, noise reduction parameters, microphone sensitivity parameters, microphone direction parameters, pitch parameters, timbre parameters, sound quality parameters, most comfortable current levels ("M" levels), threshold current levels ("T" levels), clipping levels, channel acoustic gain parameters, front and backend dynamic range parameters, current steering parameters, pulse rate values, pulse width values, frequency parameters, amplitude parameters, waveform parameters, electrode polarity parameters (i.e., anode-cathode assignment), location parameters (i.e., which electrode pair or electrode group receives the stimulation current), stimulation type parameters (i.e., monopolar, bipolar, or tripolar stimulation), burst pattern parameters (e.g., burst on time and burst off time), duty cycle parameters, spectral tilt parameters, filter parameters, and dynamic compression parameters. Sound processor 104 may also be configured to operate in accordance with one or more of the control parameters.

As shown in FIG. 1, coil 108 may be housed within headpiece 106, which may be affixed to a patient's head and positioned such that coil 108 is communicatively coupled to a corresponding coil included within auditory prosthesis 110. In this manner, control parameters and power signals may be wirelessly transmitted between sound processor 104 and auditory prosthesis 110 via communication link 118. It will be understood that data communication link 118 may include a bi-directional communication link and/or one or more dedicated uni-directional communication links. In some alternative embodiments, sound processor 104 and auditory prosthesis 110 may be directly connected with one or more wires or the like.

Auditory prosthesis 110 may include any type of implantable stimulator that may be used in association with the systems and methods described herein. For example, auditory prosthesis 110 may include an implantable cochlear stimulator. In some alternative implementations, auditory prosthesis 110 may include a brainstem implant and/or any other type of auditory prosthesis that may be implanted within a patient and configured to apply stimulation to one or more stimulation sites located along an auditory pathway of a patient.

In some examples, auditory prosthesis 110 may be configured to generate electrical stimulation representative of an audio signal detected by microphone 102 in accordance with one or more stimulation parameters transmitted thereto by sound processor 104. Auditory prosthesis 110 may be further configured to apply the electrical stimulation to one or more stimulation sites within the patient via one or more electrodes 114 disposed along lead 112. In some examples, auditory prosthesis 110 may include a plurality of independent current sources each associated with a channel defined by one or more of electrodes 114. In this manner, different stimulation current levels may be applied to multiple stimulation sites simultaneously by way of multiple electrodes 114. In such examples, auditory prosthesis system 100 may be referred to as a "multi-channel auditory prosthesis system."

To facilitate application of the electrical stimulation generated by auditory prosthesis 110, lead 112 may be inserted within a duct of the cochlea such that electrodes 114 are in communication with one or more stimulation sites within the cochlea. As used herein, the term "in communication with" refers to electrodes 114 being adjacent to, in the general vicinity of, in close proximity to, directly next to, or directly on the stimulation site. Any number of electrodes 114 (e.g., sixteen) may be disposed on lead 112 as may serve a particular implementation.

Figure 2:
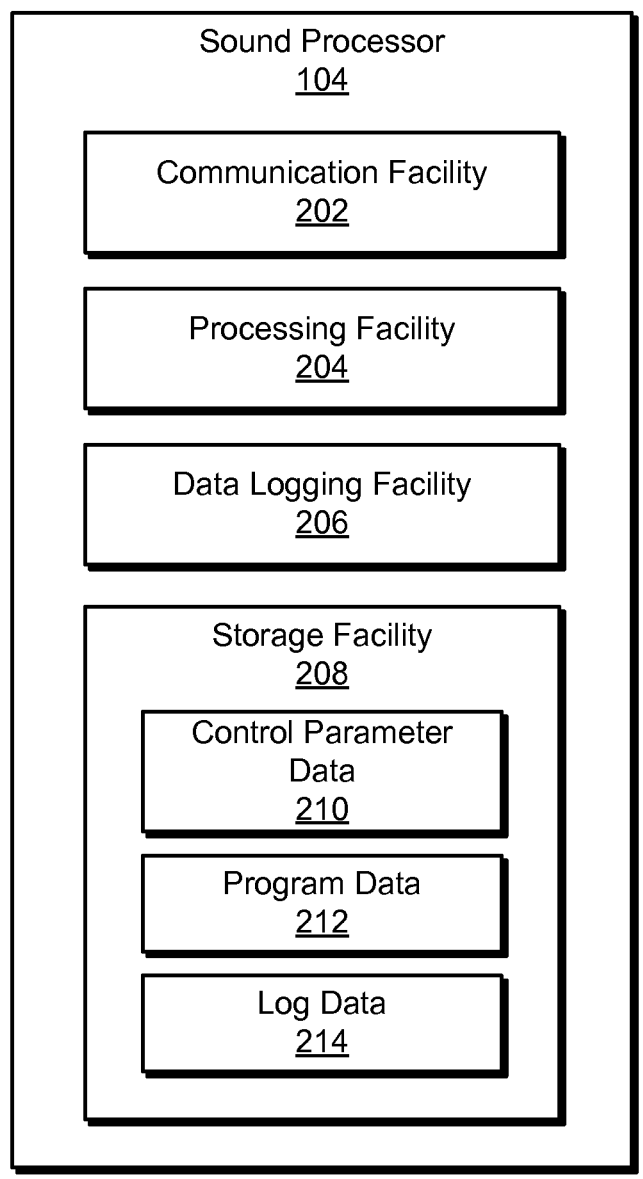
FIG. 2 illustrates exemplary components of a sound processor according to principles described herein.

FIG. 2 illustrates exemplary components of sound processor 104. As shown in FIG. 2, sound processor 104 may include a communication facility 202, a processing facility 204, a detection facility 206, and a storage facility 208, any or all of which may be in communication with one another using any suitable communication technologies. Each of these facilities may include any combination of hardware, software, and/or firmware as may serve a particular application. For example, one or more of facilities 202-208 may include a computing device or processor configured to perform one or more of the functions described herein. Facilities 202-208 will now be described in more detail.

Communication facility 202 may be configured to facilitate communication between sound processor 104 and auditory prosthesis 110. For example, communication facility 202 may include transceiver components configured to wirelessly transmit data (e.g., control parameters and/or power signals) to auditory prosthesis 110 and/or wirelessly receive data from auditory prosthesis 110.

Communication facility 202 may be further configured to facilitate communication between sound processor 104 and a fitting device configured to perform one or more fitting operations associated with auditory prosthesis system 100. For example, communication facility 202 may be configured to facilitate electrical coupling of sound processor 104 to a clinician's programming interface device in order to communicate with the fitting device.

Processing facility 204 may be configured to operate in accordance with one or more control parameters. The control parameters may be loaded onto sound processor 104 by a fitting device and/or otherwise stored within storage facility 208.

To illustrate, processing facility 204 may be configured to perform one or more signal processing heuristics on an audio signal presented to the patient. For example, processing facility 204 may perform one or more pre-processing operations, spectral analysis operations, noise reduction operations, mapping operations, and/or any other types of signal processing operations on a detected audio signal as may serve a particular implementation.

As will be described in more detail below, processing facility 204 may generate and/or adjust one or more control parameters governing an operation of sound processor 104 and/or auditory prosthesis 110 (e.g., one or more stimulation parameters defining the electrical stimulation to be generated and applied by auditory prosthesis 110) in accordance with data logged by auditory prosthesis 110. For example, processing facility 204 may adjust one or more control parameters associated with a sound processing program based on the data logged by auditory prosthesis 110.

Data logging facility 206 may be configured to log data associated with an operation of sound processor 104. For example, data logging facility 206 may perform one or more measurements and/or other procedures in order to acquire the data. Data logging facility 206 may be further configured to transmit the logged data to auditory prosthesis 110 for storage within a storage device that is a part of auditory prosthesis 110. It will be recognized that data logging facility 206 is optional and that in some examples, sound processor 104 does not include data logging facility 206 and that all of the logging is performed by auditory prosthesis 110.

Storage facility 208 may be configured to maintain control parameter data 210 representative of one or more control parameters governing an operation of sound processor 104, program data 212 representative of one or more sound processing programs loaded onto sound processor 104, and log data 214 acquired by and/or otherwise associated with data logging facility 206. Storage facility 208 may be configured to maintain additional or alternative data as may serve a particular implementation.

Figure 3:
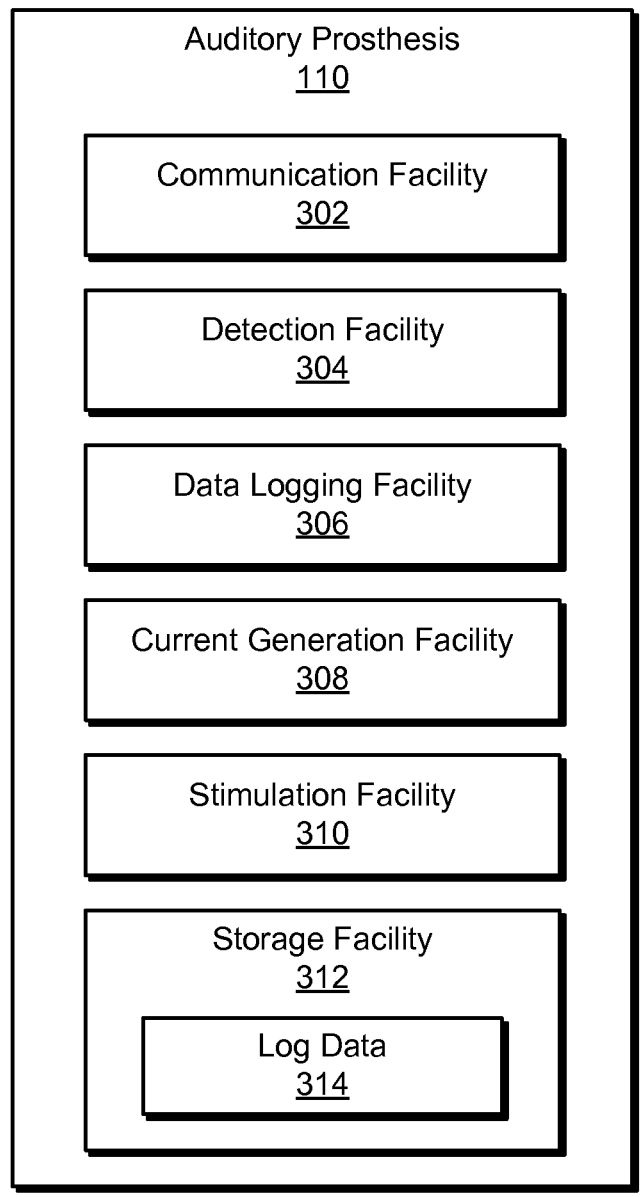
FIG. 3 illustrates exemplary components of an auditory prosthesis according to principles described herein.

FIG. 3 illustrates exemplary components of auditory prosthesis 110. As shown in FIG. 3, auditory prosthesis 110 may include a communication facility 302, a detection facility 304, a data logging facility 30 a current generation facility 308, a stimulation facility 310, and a storage facility 312, which may be in communication with one another using any suitable communication technologies. Each of these facilities may include any combination of hardware, software, and/or firmware as may serve a particular application. For example, one or more of facilities 302-312 may include a computing device or processor configured to perform one or more of the functions described herein. Facilities 302-312 will now be described in more detail.

Communication facility 302 may be configured to facilitate communication between auditory prosthesis 110 and sound processor 104. For example, communication facility 302 may include one or more coils configured to receive control signals and/or power signals from sound processor 104. Communication facility 302 may additionally or alternatively be configured to transmit one or more status signals and/or other data to sound processor 104.

Detection facility 304 may be configured to detect a communicative coupling of a sound processor to auditory prosthesis 110. For example, detection facility 304 may detect that a patient has "put on" a sound processor (e.g., placed the sound processor on or behind his or her ear), plugged a sound processor into a headpiece, or taken any other action to communicatively couple a sound processor to auditory prosthesis 110.

Detection facility 304 may be further configured to detect a communicative decoupling of a sound processor from auditory prosthesis 110. For example, detection facility 304 may detect that a patient has "taken off" a sound processor (e.g., removed the sound processor from being on or behind his or her ear), unplugged a sound processor from a headpiece, or taken any other action to communicatively decouple a sound processor from auditory prosthesis 110.

In some examples, detection facility 304 may be configured to distinguish between different sound processors that may be communicatively coupled to auditory prosthesis 110. For example, each sound processor may have a unique identifier (e.g., a unique serial number). Detection facility 304 may be configured to identify the unique identifier and notify data logging facility 306 accordingly.

Data logging facility 306 may be configured to log data associated with an operation of a sound processor while the sound processor is communicatively coupled to auditory prosthesis 110. Data logging facility 306 may log the data in any suitable manner. For example, data logging facility 306 may receive log data acquired by the sound processor and store the log data within a storage device (e.g., a storage device implementing storage facility 312) that is a part of auditory prosthesis 110. Additionally or alternatively, data logging facility 306 may monitor the operation of the sound processor and generate the log data based on the monitoring. To illustrate, data logging facility 306 may monitor a usage time associated with a particular sound processor and generate data representative of the usage time.

In some examples, data logging facility 306 may transmit logged data associated with an operation of a sound processor to the sound processor so that the sound processor may process the logged data. For example, the sound processor may adjust one or more control parameters in accordance with the logged data. Additionally or alternatively, data logging facility 306 may transmit the logged data to a fitting device or the like so that the fitting device may perform one or more fitting operations in accordance with the logged data.

As mentioned, a user may interchangeably connect various sound processors to auditory prosthesis 110. Hence, data logging facility 306 may be configured to log data associated with an operation of any sound processor that is communicatively coupled to auditory prosthesis 110.

For example, data logging facility 306 may log data associated with an operation of a first sound processor while the first sound processor is communicatively coupled to auditory prosthesis 110. The first sound processor may then be removed and replaced with a second sound processor. Data logging facility 306 may then log data associated with an operation of the second sound processor while the second sound processor is communicatively coupled to auditory prosthesis 110.

In some examples, data logging facility 306 may be configured to maintain distinct sets of logged data each associated with a different sound processor separate one from another. For example, data logging facility 306 may maintain a first set of logged data associated with a first sound processor separate from a second set of logged data associated with a second sound processor. As will be described in more detail below, the separate sets of logged data may be used (e.g., by a fitting device) to compare a relative performance of the first and second sound processors. The distinct sets of logged data may be separately maintained by storing the sets of logged data in distinct locations, indexing or tagging the distinct sets of logged data in a distinguishing manner, and/or otherwise marking the distinct sets of logged data as being associated with their respective sound processors.

In some alternative examples, data logging facility 306 does not maintain distinct sets of logged data associated with different sound processors. Rather, data logging facility 306 may be configured to maintain a single set of logged data that corresponds to any sound processor that is communicatively coupled to auditory prosthesis 110.

In some examples, data logging facility 306 may be configured to transmit logged data to a sound processor that is communicatively coupled to auditory prosthesis 110 for processing by the sound processor. For example, data logging facility 306 may log data associated with an operation of a particular sound processor while the sound processor is communicatively coupled to auditory prosthesis 110. Data logging facility 306 may then transmit the logged data to the sound processor so that the sound processor may analyze the logged data and adjust one or more control parameters and/or otherwise modify a manner in which the sound processor and/or auditory prosthesis 110 operates.

Logged data associated with a particular sound processor may also be transmitted by data logging facility 306 to a different sound processor for processing by that sound processor. For example, data logging facility 306 may log data associated with an operation of a first sound processor while the first sound processor is communicatively coupled to auditory prosthesis 110. The first sound processor may then be removed and replaced with a second sound processor. Data logging facility 306 may then transmit the log data associated with the first sound processor to the second sound processor so that the second sound processor may analyze the logged data and adjust one or more control parameters and/or otherwise modify a manner in which the second sound processor and/or auditory prosthesis 110 operates. In this manner, the second sound processor may utilize already acquired log data in order to more efficiently and effectively optimize a manner in which the second sound processor operates.

To illustrate, data logging facility 306 may log data representative of one or more sound levels associated with a particular sound processing program being executed by a first sound processor that is communicatively coupled to auditory prosthesis 110. The first sound processor may then be removed and replaced with a second sound processor. By analyzing the logged data, the second sound processor may automatically adjust one or more sound levels to match those represented in the logged data so that the user does not have to adjust them himself or herself.

Current generation facility 308 may be configured to generate stimulation current in accordance with one or more stimulation parameters received from sound processor 104. To this end, current generation facility 308 may include one or more current generators and/or any other circuitry configured to facilitate generation of stimulation current. For example, current generation facility 308 may include an array of independent current generators each corresponding to a distinct electrode or channel.

Stimulation facility 310 may be configured to facilitate application of the stimulation current generated by current generation facility 308 to one or more stimulation sites within the patient in accordance with one or more stimulation parameters received from sound processor 104.

Storage facility 312 may be configured to maintain log data 314 generated or otherwise maintained by data logging facility 306. Storage facility 312 may be configured to maintain additional or alternative data as may serve a particular implementation. To this end, storage facility 312 may be implemented by any suitable storage device included within auditory prosthesis 110. For example, storage facility 312 may be implemented by a hard drive, a flash drive, random access memory ("RAM"), dynamic RAM ("DRAM"), and/or other non-volatile and/or volatile data storage units.

Figure 4:
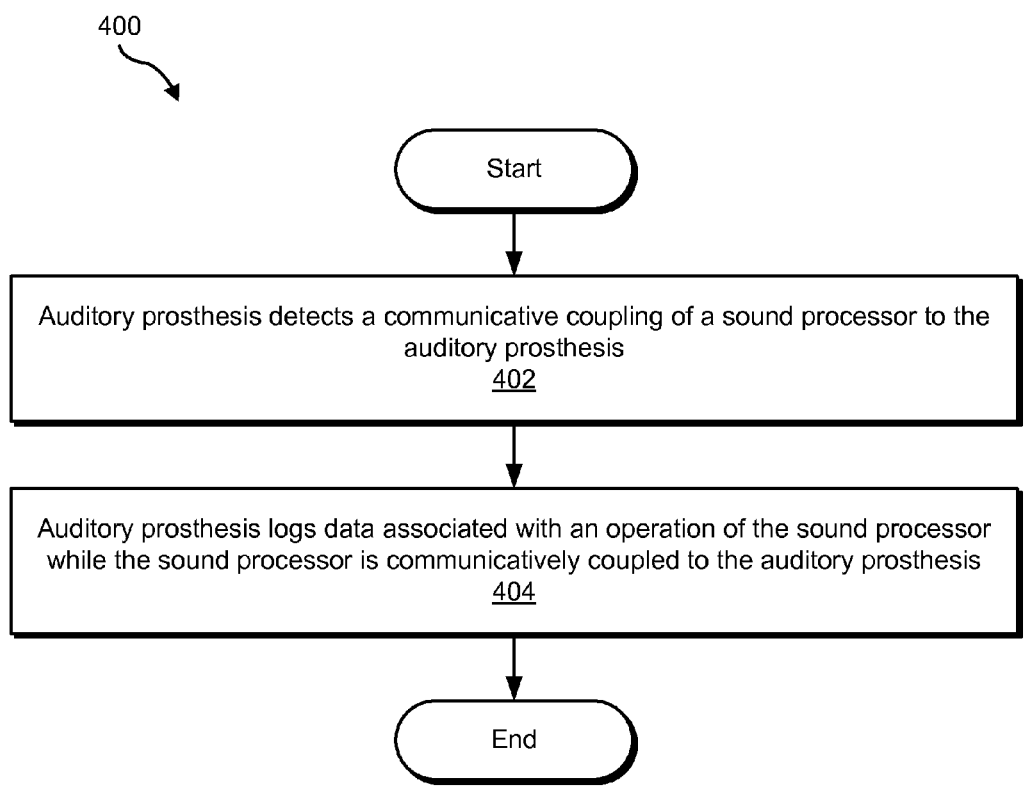
FIG. 4 illustrates an exemplary method of logging data associated with an operation of a sound processor according to principles described herein.

FIG. 4 illustrates an exemplary method 400 of logging data associated with an operation of a sound processor. While FIG. 4 illustrates exemplary steps according to one embodiment, other embodiments may omit, add to, reorder, combine, and/or modify any of the steps shown in FIG. 4. One or more of the steps shown in FIG. 4 may be performed by any component or combination of components of auditory prosthesis 110.

In step 402, an auditory prosthesis detects a communicative coupling of a sound processor to the auditory prosthesis. As described herein, the auditory prosthesis may be configured to be implanted within a patient and the sound processor may be configured to be located external to the patient. Step 402 may be performed in any of the ways described herein.

In step 404, the auditory prosthesis logs data associated with an operation of the sound processor while the sound processor is communicatively coupled to the auditory prosthesis. The auditory prosthesis may log the data in any of the ways described herein.

Figure 5:
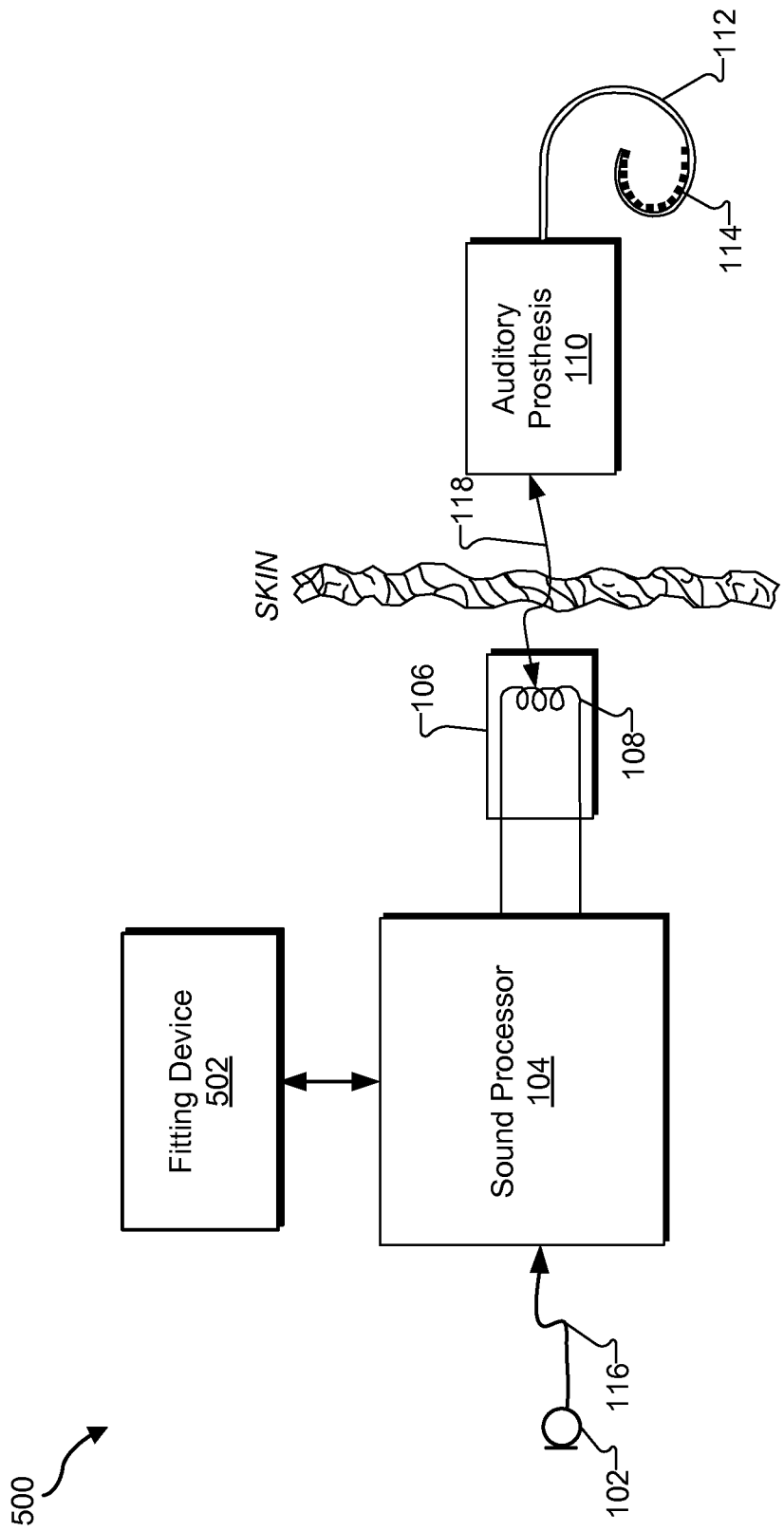
FIG. 5 illustrates an exemplary configuration wherein a fitting device is communicatively coupled to a sound processor that is communicatively coupled to auditory prosthesis according to principles described herein.

As mentioned, log data maintained by auditory prosthesis 110 may be utilized by a fitting device to perform various fitting operations associated with one or more sound processors and/or auditory prosthesis 110. FIG. 5 illustrates an exemplary configuration 500 wherein a fitting device 502 is communicatively coupled to a sound processor 104 that is communicatively coupled to auditory prosthesis 110. Fitting device 502 may implemented by any suitable combination of computing and communication devices including, but not limited to, a fitting station, a personal computer, a laptop computer, a handheld device, a mobile device (e.g., a mobile phone), and/or any other suitable component as may serve a particular implementation.

To illustrate, auditory prosthesis 110 may transmit log data associated with sound processor 104 to fitting device 502. The log data may be transmitted in any suitable manner. For example, auditory prosthesis 110 may transmit the log data to fitting device 502 by way of sound processor 104. Fitting device 502 may utilize the log data to perform one or more testing procedures, adjust one or more control parameters associated with sound processor 104, create and load a new sound processing program onto sound processor 104, and/or perform any other fitting operation.

As an example, auditory prosthesis 110 may log data associated with an operation of sound processor 104 for a predetermined amount of time preceding a visit by the patient to an audiologist's clinic. During the visit, the audiologist may utilize fitting device 502 to request and acquire the log data. The audiologist may then use fitting device 502 to analyze the log data and determine whether various control parameters need to be adjusted.

In cases where multiple sound processors have been communicatively coupled to auditory prosthesis 110, the log data acquired by fitting device 502 from auditory prosthesis 110 may be used by fitting device 502 to compare a relative performance of the multiple sound processors. For example, fitting device 502 may determine a relative usage of the sound processors (i.e., how much time each sound processor was communicatively coupled to auditory prosthesis 110 during a particular time period), a relative performance of different sound processing programs being executed by the multiple sound processors, and/or any other comparative metric as may serve a particular implementation.

In the preceding description, various exemplary embodiments have been described with reference to the accompanying drawings. It will, however, be evident that various modifications and changes may be made thereto, and additional embodiments may be implemented, without departing from the scope of the invention as set forth in the claims that follow. For example, certain features of one embodiment described herein may be combined with or substituted for features of another embodiment described herein. The description and drawings are accordingly to be regarded in an illustrative rather than a restrictive sense.

What is claimed is:

1. A method comprising:
   detecting, by an auditory prosthesis configured to be implanted in a patient, a communicative coupling of a first sound processor to the auditory prosthesis;
   logging, by the auditory prosthesis, data associated with an operation of the first sound processor while the first sound processor is communicatively coupled to the auditory prosthesis;
   detecting, by the auditory prosthesis, a communicative decoupling of the first sound processor from the auditory prosthesis and a communicative coupling of a second sound processor to the auditory prosthesis;
   logging, by the auditory prosthesis, additional data associated with an operation of the second sound processor while the second sound processor is communicatively coupled to the auditory prosthesis;
   storing, by the auditory prosthesis, the logged data and the additional logged data in a storage device that is a part of the auditory prosthesis; and
   tagging the stored logged data as being associated with the first sound processor and the stored additional logged data as being associated with the second sound processor in a manner that maintains the stored logged data and the stored additional logged data separate one from another.

2. The method of claim 1, further comprising transmitting, by the auditory prosthesis while the first sound processor is communicatively coupled to the auditory prosthesis, the logged data to the first sound processor for processing by the first sound processor.

3. The method of claim 2, further comprising adjusting, by the first sound processor, one or more control parameters associated with the operation of the first sound processor or an operation of the auditory prosthesis in accordance with at least one of the logged data and the additional logged data.

4. The method of claim 1, further comprising transmitting, by the auditory prosthesis, the logged data and the additional logged data to a fitting device located external to the patient.

5. The method of claim 4, further comprising comparing, by the fitting device, a relative performance of the first sound processor and the second sound processor based on the logged data and the additional logged data.

6. The method of claim 1, wherein the logging of the data associated with the operation of the first sound processor comprises:
- receiving, by the auditory prosthesis, the data associated with the operation of the first sound processor from the first sound processor; and
- storing, by the auditory prosthesis, the data within the storage device that is a part of the auditory prosthesis.

7. The method of claim 1, wherein the logging of the data associated with the operation of the first sound processor comprises:
- monitoring, by the auditory prosthesis, the operation of the first sound processor; and
- generating, by the auditory prosthesis based on the monitoring, the data representative of the operation of the first sound processor.

8. The method of claim 1, further comprising logging, by the auditory prosthesis, data associated with an operation of the auditory prosthesis.

9. The method of claim 1, wherein the logged data and the additional logged data comprise at least one of volume control data, battery life data, usage time data, sound level data, sound processing program usage data, measurement data, testing data, troubleshooting data, acoustic scene data, operating status data, and control parameter data.

10. The method of claim 1, further comprising transmitting, by the auditory prosthesis while the second sound processor is communicatively coupled to the auditory prosthesis, the logged data associated with the operation of the first sound processor to the second sound processor for processing by the second sound processor.

11. An auditory prosthesis configured to be implanted in a patient and comprising:
- a detection facility and a data logging facility communicatively coupled to the detection facility, wherein:
  - the detection facility detects a communicative coupling of a first sound processor to the auditory prosthesis;
  - the data logging facility logs data associated with an operation of the first sound processor while the first sound processor is communicatively coupled to the auditory prosthesis;
  - the detection facility detects a communicative decoupling of the first sound processor from the auditory prosthesis and a communicative coupling of a second sound processor to the auditory prosthesis;
  - the data logging facility logs additional data associated with an operation of the second sound processor while the second sound processor is communicatively coupled to the auditory prosthesis;
  - the data logging facility stores the logged data and the additional logged data in a storage device that is a part of the auditory prosthesis; and
  - the data logging facility tags the stored logged data as being associated with the first sound processor and the stored additional logged data as being associated with the second sound processor in a manner that maintains the stored logged data and the stored additional logged data separate one from another.

12. The auditory prosthesis of claim 11, wherein the data logging facility transmits, while the first sound processor is communicatively coupled to the auditory prosthesis, the logged data to the first sound processor for processing by the first sound processor.

13. The auditory prosthesis of claim 11, wherein the data logging facility transmits, while the second sound processor is communicatively coupled to the auditory prosthesis, the logged data associated with the operation of the first sound processor to the second sound processor for processing by the second sound processor.

14. A system comprising:
- a sound processor configured to be located external to a patient and operate in accordance with one or more control parameters; and
- an auditory prosthesis communicatively coupled to the sound processor and configured to be implanted within the patient;
- wherein the auditory prosthesis
  - detects a communicative coupling of the sound processor to the auditory prosthesis,
  - logs data associated with an operation of the sound processor while the sound processor is communicatively coupled to the auditory prosthesis,
  - logs additional logged data associated with an operation of an additional sound processor that was communicatively coupled to the auditory prosthesis prior to the sound processor being communicatively coupled to the auditory prosthesis,
  - stores the logged data and the additional logged data in a storage device that is a part of the auditory prosthesis; and
- tags the stored logged data as being associated with the sound processor and the stored additional logged data as being associated with the additional sound processor in a manner that maintains the stored logged data and the stored additional logged data separate one from another.

15. The system of claim 14, wherein:
the auditory prosthesis further transmits the logged data to the sound processor; and
the sound processor is further configured to modify a manner in which the sound processor operates in accordance with the logged data.

16. The system of claim 14, wherein:
the sound processor is further configured to modify a manner in which the sound processor operates in accordance with the additional logged data.

17. The system of claim 14, wherein the auditory prosthesis transmits the additional logged data to the sound processor.

* * * * *